United States Patent [19]

Brummer et al.

[11] Patent Number: 5,656,283
[45] Date of Patent: Aug. 12, 1997

[54] IN-SITU LYOPHILIZATION OF VAGINAL SUPPOSITORY IN UNIT DOSE APPLICATOR AND RESULTANT PRODUCT

[75] Inventors: Barbara Brummer, Upper Montclair; Paul Swick, Lebanon, both of N.J.; Martin Link, Doylestown, Pa.; William Hart, Freehold, N.J.

[73] Assignee: Ortho Pharmaceutical Corporation, Raritan, N.J.

[21] Appl. No.: 495,738

[22] Filed: Jun. 8, 1995

[51] Int. Cl.⁶ .................. A61F 15/00; A61F 13/30
[52] U.S. Cl. .................. 424/433; 424/430; 424/431; 427/2.14; 514/965; 514/967; 604/15; 604/288
[58] Field of Search .................. 424/430, 431, 424/433; 206/529; 427/2.14; 514/965, 967; 604/14, 15, 55, 59, 275, 279, 288

[56] References Cited

U.S. PATENT DOCUMENTS

| | | | |
|---|---|---|---|
| D. 289,691 | 5/1987 | Rex | D24/141 |
| 3,234,091 | 2/1966 | Lang et al. | 167/64 |
| 3,595,233 | 7/1971 | Fuchslocher et al. | 604/15 |
| 3,667,465 | 6/1972 | Voss | 604/59 |
| 3,749,093 | 7/1973 | Bloom | 604/14 |
| 3,812,250 | 5/1974 | Aubert et al. | 424/659 |
| 3,830,236 | 8/1974 | Hanke | 604/14 |
| 3,831,605 | 8/1974 | Fournier | 604/17 |
| 3,884,233 | 5/1975 | Summey | 604/15 |
| 4,265,875 | 5/1981 | Byrne et al. | 424/436 |
| 4,292,300 | 9/1981 | Byrne et al. | 424/436 |
| 4,361,150 | 11/1982 | Voss | 604/15 |
| 4,406,883 | 9/1983 | Byrne et al. | 514/125 |
| 5,213,566 | 5/1993 | Weissenburger | 604/14 |
| 5,330,427 | 7/1994 | Weissenburger | 604/14 |
| 5,346,468 | 9/1994 | Campion et al. | 604/13 |

FOREIGN PATENT DOCUMENTS

| | | |
|---|---|---|
| 0 044 624A1 | 1/1982 | European Pat. Off. ........ A61L 15/00 |
| 0 587 431 A1 | 3/1994 | European Pat. Off. ........ A61K 9/12 |
| 0 643 963 A2 | 3/1995 | European Pat. Off. ........ A61K 9/12 |
| 0 438 358A1 | 7/1991 | France ........ A61K 9/16 |

*Primary Examiner*—Melvyn I. Marquis
*Assistant Examiner*—Robert H. Harrison

[57] ABSTRACT

This invention relates to a novel method of manufacturing a lyophilized suppository composition wherein said suppository is made in situ in an applicator cartridge.

24 Claims, 5 Drawing Sheets

IN-SITU LYOPHILIZATION OF VAGINAL SUPPOSITORY IN UNIT DOSE APPLICATOR AND RESULTANT PRODUCT

FIELD OF INVENTION

This invention relates to methods of making a lyophilized vaginal suppository and to the products made according to said methods. More particularly, this invention relates to novel methods and products which minimize the necessity for handling the products during preparation and which aid in the ease of handling and application by the user.

U.S. Pat. No. 5,354,558 and copending patent applications Ser. Nos. 08/104,785 U.S. Pat. No. 5,458,884 and 08/252,504, now abandoned which are hereby incorporated herein by reference, describe the preparation of freeze-dried, or lyophilized, vaginal suppositories. In accordance with the patent, the suppositories were dried in molds or plastic unit dosage shells. In the former case, the individual manufacturing the suppositories was required to handle the product during the manufacturing process. In the latter case, the consumer would be required to remove the product from the package and place it into an applicator for delivery. Unnecessary handling of vaginal suppositories can be unsanitary and not healthful for the consumer in that it can inoculate the suppository with bacterial flora which can then be introduced into the vagina or other body cavity and cause additional infection.

It would, therefore, be desirable to create a method for making vaginal suppositories or suppositories for use in other body cavities which minimizes handling during the manufacturing process and by consumers during use.

It is an object of this invention to provide a method for making vaginal suppositories which does not require handling during the manufacturing process.

It is another object of this invention to provide a method for making vaginal suppositories which results in a product which need not be handled by consumers during application.

Another object of this invention is to provide a product which is easy to insert into the vaginal cavity and which does not require handling prior to insertion.

Additional objects of this invention will become evident in the ensuing description.

SUMMARY OF THE INVENTION

Figure 1:
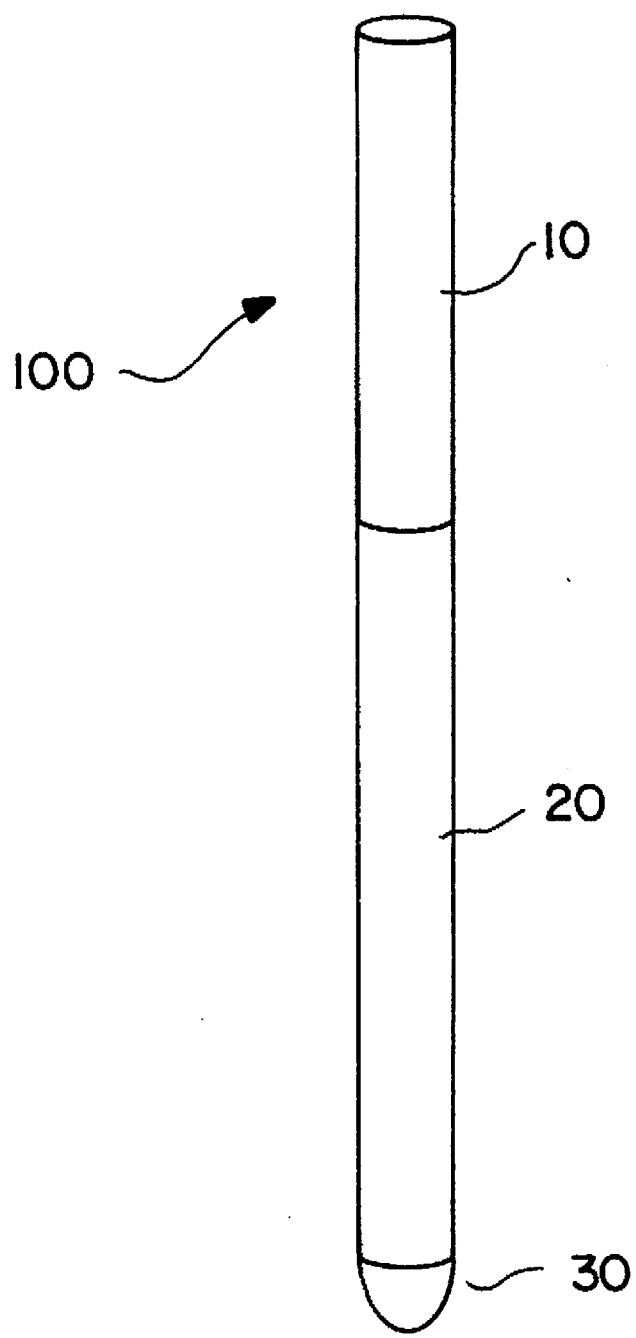
FIG. 1 depicts a plan view of an in-situ lyophilized suppository product having a plunger, barrel and suppository formed therein.

This invention relates to a process for forming vaginal suppositories or other suppository which minimizes the handling of the medicament during manufacture and use by filling unit dose cartridges with a liquid formulation containing medicament and freeze-drying, or lyophilizing, the formulation in the unit dose cartridges. The filled lyophilized cartridges can then be wrapped and packaged. When the cartridges are to be used, the consumer can simply remove them from the package, insert the cartridge into the vagina and manipulate it to deliver the suppository.

The cartridge can be manufactured so as to provide a separate plunger mechanism which can be used for application and insertion, or it can be pre-assembled such that the plunger mechanism is inserted in the cartridge prior to wrapping and is ready to use upon removable of the overwrap.

The products of this invention have several attributes which represent improvements over prior vaginal suppository products. For example, cartridges can be filled with liquid product and frozen in the lyophilizer, thus ensuring ease of manufacture. The product can then be freeze-dried directly in the cartridge, without requiring that it be inserted later, thus simplifying the manufacturing process. Furthermore, plastic or cardboard cartridge materials may be used and function in a similar manner. Dried product is easily ejected from the cartridge using the plunger, thus ensuring that the entire suppository is inserted without damage to the product or retention on the walls of the cartridge.

DETAILED DESCRIPTION OF THE PREFERRED EMBODIMENTS

The products of this invention are composed of a unit dose cartridge and a suppository formulation. Optionally, a plunger may be inserted into the cartridge to make a pre-assembled applicator.

The lyophilized vaginal suppository of this invention generally contains an active ingredient, such as an antifungal medication or a spermicide. Preferably, the antifungal medication may be miconazole nitrate, econazole, terconazole, ketoconazole, saperconazole, itraconazole, tioconazole, butaconazole, and other imidizoles present either as the free base or as a salt of an anion, e.g., nitrate.

In order to produce a lyophilized vaginal suppository, an initial aqueous dispersion must be provided, which will then be freeze-dried. Thus, an aqueous dispersion should be formed comprising at least one, and preferably several, water-soluble polymers and an active ingredient. The term "aqueous dispersion" as used herein is meant to include dispersions (including solutions) in which the solvent is water and optionally, water-miscible liquids.

Preferably, the polymer is initially added to the solvent and dispersed, followed by addition and dispersion of the active ingredient. If necessary, heat can be applied to the mixture to facilitate dispersion.

Cellulose, cellulose ethers, derivatives thereof and polymers of the type set forth in U.S. Pat. No. 4,615,697, issued to Robinson, and commercially available under the generic name "polycarbophil" are suitable for use in the present invention. Other suitable polymers include polycarboxylated vinyl polymers, including polyacrylic acid polymers, polyacrylic acid polymers that are lightly crosslinked with a polyalkenyl polyether, such as those commercially available from B. Goodrich, Cincinnati, Ohio, under the trademarks Carbopol®434, 934P, 940 and 941, polysaccharide gums (such as natural plant exudates including e.g., karaya gum, ghatti gum and the like), and seed gums (including e.g., guar gum, locust bean gum, psyllium seed gum and the like). Crosslinked alginate gum gels of the type described in U.S. Pat. No. 3,640,741 to Etes are also suitable.

Preferably, the polymer is selected from the group consisting of polyurethanes, gelatins, celluloses and cellulose ethers, including hydroxypropylmethylcellulose, sodium carboxymethylcellulose, methylcellulose, hydroxyethylcellulose, hydroxypropylcellulose, hydroxyethylmethylcellulose, hydroxyethylethylcellulose, hydroxypropylethylcellulose, carbopol, polyvinyl alcohol and derivatives thereof, dextran, chitosan and its derivatives, starch and its derivatives, polyacrylamides, polyacrylates, agar, collagen, fibronectin, alginic acid, pectin, hyaluronic acid or mixtures thereof.

Compositions comprised of cellulose ethers are especially preferred. In particular, it has been found that suppositories comprising hydroxypropylmethylcellulose, a mixture of gelatin and hydroxypropylmethylcellulose or a mixture of hydroxypropylmethylcellulose and sodium carboxylmethylcellulose possess excellent qualities, including good adherent properties.

Certain polymers, such as cellulose ethers generally and hydroxypropylmethylcellulose (for example, Methocel E50LV Premium commercially available from Dow Corporation of Midland, Mich.) in particular, may be employed to provide liquid foams and formulations having good stability and structural integrity, and dry foams and formulations with desirable softness. Other polymers, like gelatin, may be incorporated in the suppositories of the invention to make them sufficiently rigid so that they can be inserted with an applicator without breaking or fracturing. One skilled in the art can readily determine the polymeric ingredients and their amounts that result in a device having the preferred combination of suitable properties.

Typically, polymer is added to the dispersion at a concentration of about 1% to about 20% (by weight of the total dispersion including active ingredient), preferably about 2 to about 16%, even more preferably about 2 to about 7%. At lower concentrations, there may be insufficient polymer to prepare a sturdy end-product, whereas at higher concentrations, the dispersion may be too viscous to process under normal conditions. However, it is not necessary in some end-uses to have a foaming suppository, in which case this product may be acceptable, as well as other formulations which may not foam.

The active ingredient may be provided in the dispersion at a concentration of about 1% to about 25% (by weight of the total dispersion) with about 5% to about 15% being preferred. The active ingredient may be present at from about 20% to about 95% by weight of the (dry) suppository, with about 50% to about 80% by weight being preferred.

However, any medicament or formulation which is dispersible in water in combination with a water-soluble polymer and lyophilizable may be conveniently used in the methods and products of this invention. For example, medicaments such as those set forth in U.S. Pat. No. 4,948,580, which is hereby incorporated by reference, may be used, incluidng antifungal agents, antibacterial agents, anti-cancer agents, anti-inflammatory agents, antiseptics, and the like.

The cartridge and plunger may be constructed of cardboard or a moldable plastic. The plastic may be coated or uncoated, as may be cardboard. Either rigid or flexible plastics may be used, depending on the preference of the manufacturer. For example, a rigid plastic such as polystyrene or polycarbonate may be useful in making the cartridge and plunger of the products of this invention. However, flexible plastics such as polyvinylchloride may also be useful. Even moldable metals such as aluminum may be useful. Preferably, cardboard is used due to its ease of use, low cost and environmentally safe attributes. Furthermore, there are currently cardboard applicators on the market.

In the process of this invention, the cartridges are inserted into a metal mesh or into a metal or plastic mold prior to filling. The cartridges may be plugged, if inserted into mesh, so as to maintain the liquid composition in the cartridge prior to freeze-drying. The plug may be made of plastic, cardboard or rubber. If inserted into a female mold, however, plugging is unnecessary. The liquid composition containing the active ingredient, water and water-soluble polymer is then poured into the cartridges. The filled cartridges are than placed in a freeze-drier such that the composition is made solid. The cartridges can then be removed from the mesh or mold and assembled into an applicator for use.

Initially, prior to freeze-drying, the cartridges can be held in position in the freeze-drier by inserting them in a metal mesh wherein the base of the cartridge is plugged with a stopper. A preferred approach is to place the cartridges in molds such that the internal cavity of the mold provides the sealing capability and stability for the cartridge. The mold can be constructed from moldable or machinable plastics such as polystyrene, polycarbonate, polyethylene, polyvinylchloride, Teflon* (available from E. I. duPont de Nemours of Wilmington, Del.) brand of polytetrafluoroethylene or related fluoropolymers. The mold may also be made of aluminum or other formable or machinable metals.

FIG. 1 depicts an in-situ formed suppository in an applicator 100 consisting of a plunger 10, barrel 20 and suppository 30. Suppository 30 has been lyophilized insitu in barrel 20 in accordance with the method of this invention.

Figure 2:
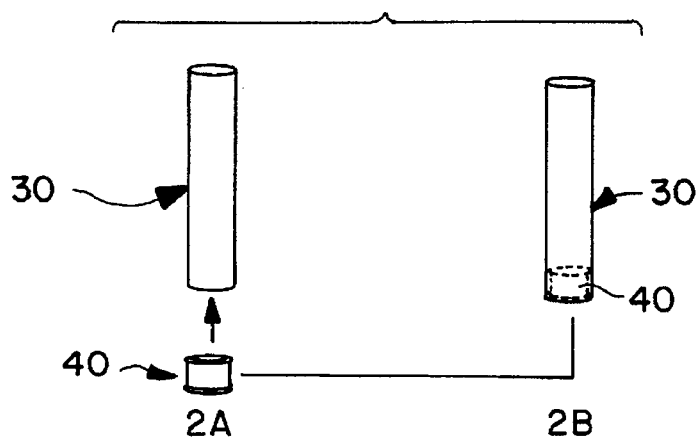
FIGS. 2A and 2B depict a plan view and a cross-sectional view of a cartridge and plug for forming a suppository product according to this invention.
Figure 3A:
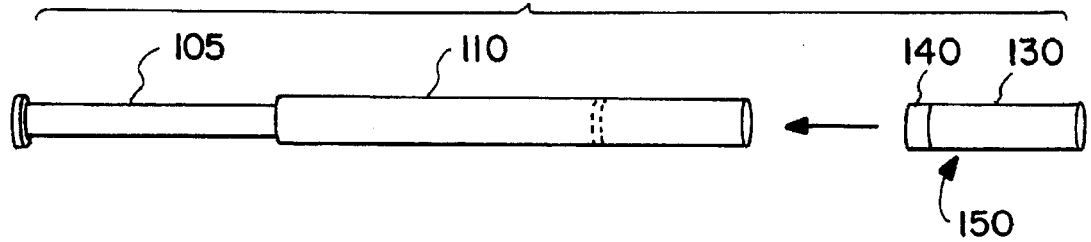
FIGS. 3A and 3B depict a plan view and cross-section of a cartridge, applicator barrel, plunger, plug and suppository in accordance with this invention.
Figure 3B:
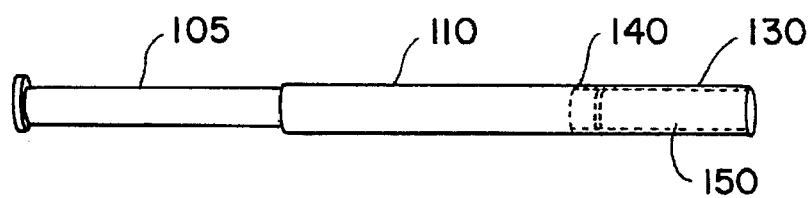

FIGS. 2A and 2B depict a cylindrical cartridge 30 which can be inserted into a metal mesh tray prior to filling. Plug 40 should be inserted into cartridge 30 prior to filling so as to provide a base to retain filled product in cartridge 30 prior to lyophilization. FIGS. 3A and 3B depict an applicator barrel 110 into whcih cartridge 150 can be inserted after lyophilization. Plunger 105 can be inserted into the end opposite the end into which cartridge 150 is inserted. Cartridge 150 contains plug 140 and active ingredient 130.

Figure 4A:
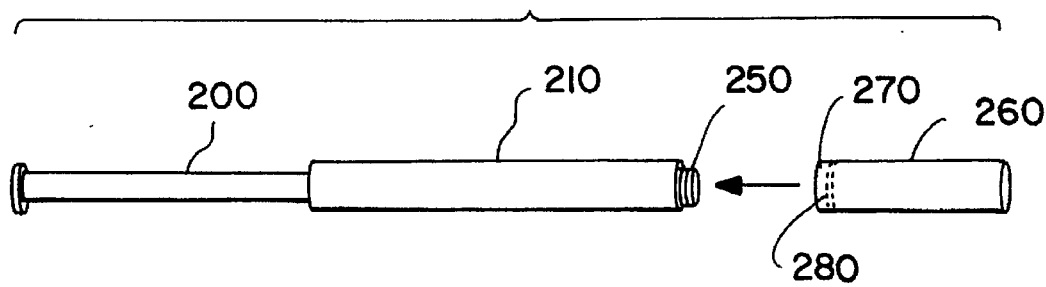
FIGS. 4A and 4B depict a plunger, screw-bottomed applicator barrel, cartridge, plug and suppository in accordance with this invention.
Figure 4B:
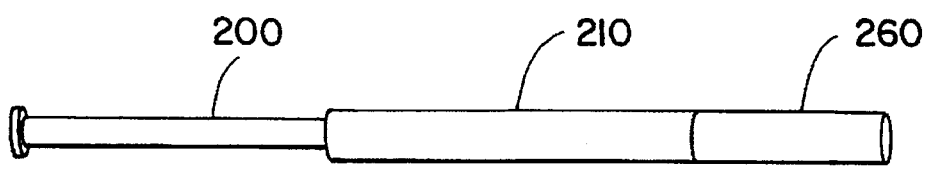

FIGS. 4A and 4B depict an applicator barrel 210 and plunger 200. Barrel 210 has screw threading 250 on the end fashioned for insertion into the body. Screw threading 250 is fasioned to receive cartridge 260, which contains plug 270. Plug 270 has screw threading 280 which is fashioned to be inserted and screwed into barrel screw threading 250.

Figure 5A:
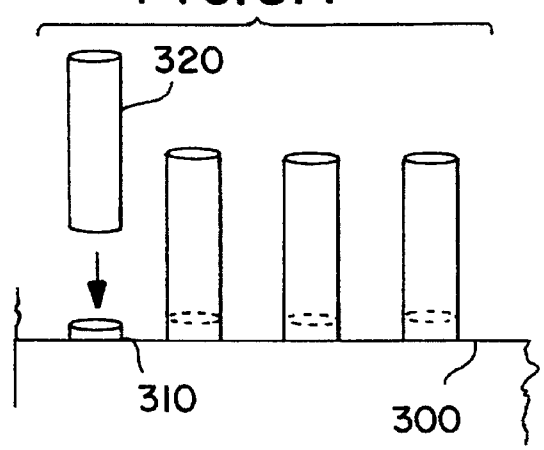
FIGS. 5A and 5B depict a lan view of a formation tray, plugs and filled and unfilled cartridges in accordance with this invention.
Figure 5B:
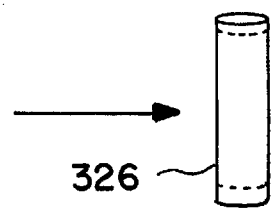

FIGS. 5A and 5B depict a formation tray 300 into which plugs 310 have been inserted. Cartridges 320 are then inserted over plugs 310, the aqueous formulation pumped into cartridges 320 and the products freeze-dried, resulting in filled cartridge 326.

Figure 6A:
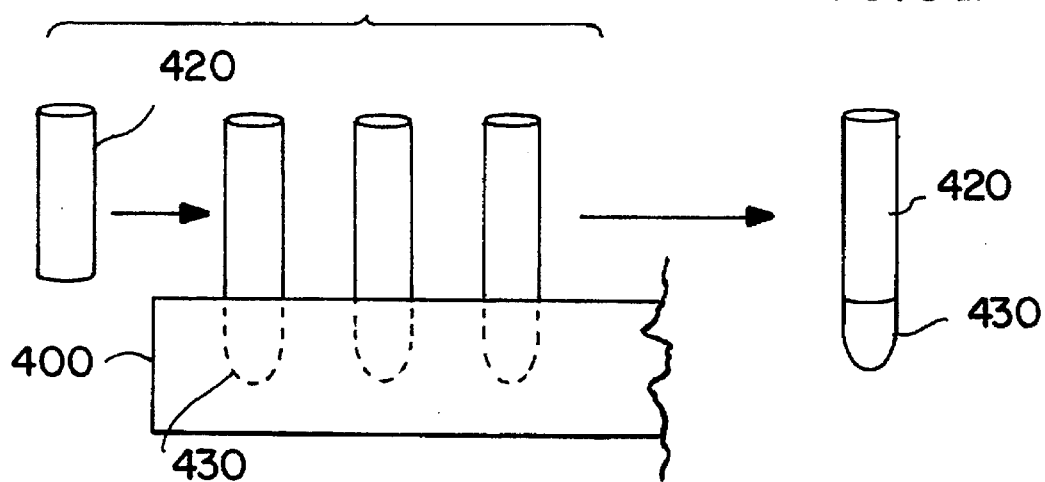
FIGS. 6A and 6B depict a plan view of a metal or plastic mold and filled and unfilled cartridges.
Figure 6B:
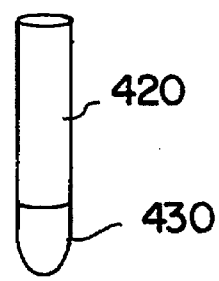

FIGS. 6A and 6B depict metal or plastic mold 400 into which empty cartridges 420 are inserted prior to filling. Cartridges 420 are filled with aqueous formulation and lyophilized. FIG. 6B depicts cartridge 420 with solid freeze-dried suppository 430, which is ready for use without the need for filling an applicator.

Figure 7:
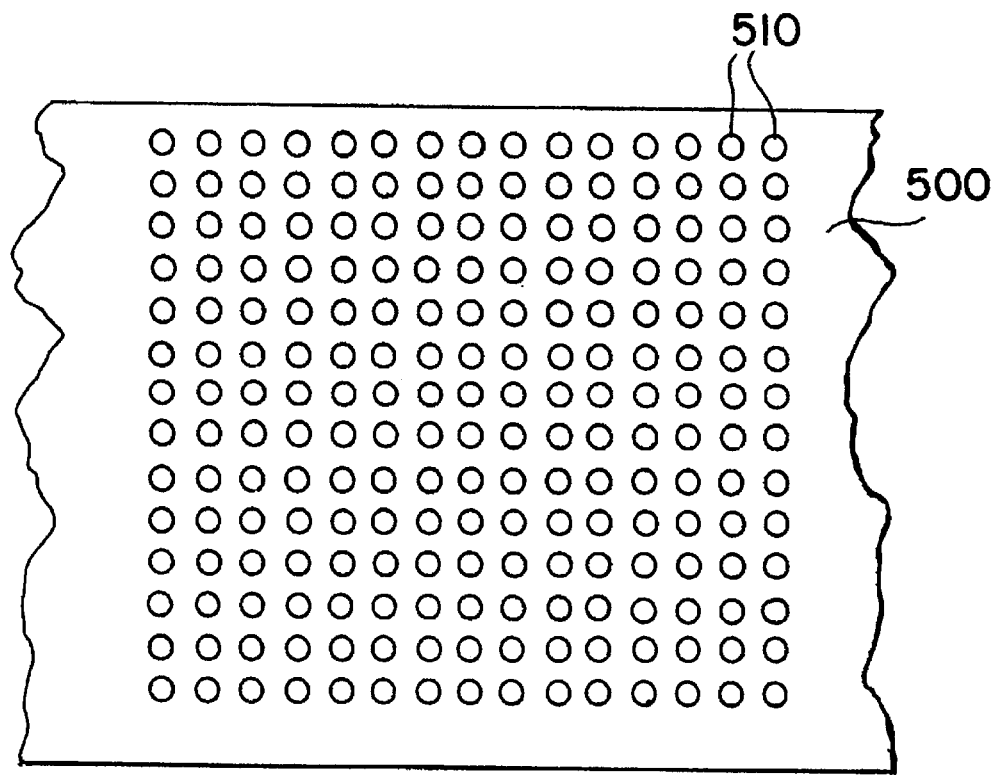
FIG. 7 depicts a plan view of a metal or plastic mold formation tray for making suppositories according to this invention.
Figure 8:
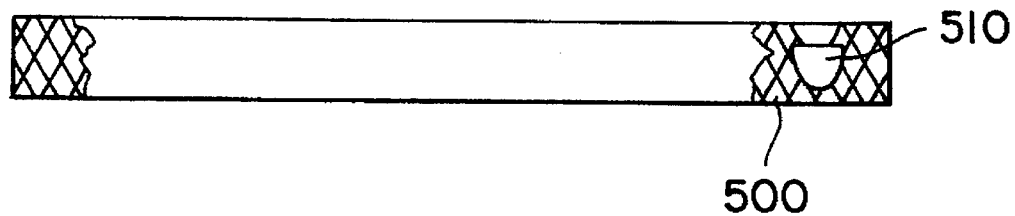
FIG. 8 depicts a cross-sectional view of a metal or plastic mold formation tray for making suppositories according to this invention.

FIG. 7 depicts formation tray 500 which is a metal or plastic mold having bullet-nosed depressions 510. FIG. 8 depicts a cross-section of tray 500 and one of depressions 510, indicating the bullet-nosed shape of depression 510.

The internal cavity of the mold is preferably a cylindrical shape or a bullet-nose shape. The bullet shape is more preferred due to the fact that, during the filling procedure, the liquid will not leak past the cardboard in the bullet-nosed mold because the cartridge is wedged more tightly in and further into a bullet-shaped mold. In contrast, in the cylindrical cavity mold, liquid is more likely to leak due to the geometry of the hole into which the cartridge is placed. Once dried, the product releases more easily and leaves less "flash" on the cardboard and in the mold. Cleanup of molds and aesthetic quality of the product is significantly better.

Preferably, the mold should have a release surface which enhances the ability of the molded product to be released from the mold, such as a lubricant material, e.g., silicone or the like. The lubricant can be sprayed onto the surface of the mold to enable quick release of final product from the mold. Other release compositions include talc or other fine powders or the like. More preferably, the coating is a permanent, abrasion- and chemical-resistant coating that complies with FDA requirements for food contact. For example, a preferably coating can be Teflon® FEP or Teflon® ceramic Reinforced coating (Silverstone Supra®, available from E. I. duPont de Nemours of Wilmington, Del.). Others include Sanford Hardlube® products, which consist of a hard anodized coating of aluminum oxide impregnated with Teflon® PTFE applied to a metal surface (available from Titanium Finishing Company, East Greenville, Pa.). Most preferably, the molds should be composed of aluminum coated with Nituff® (available from Nimet Industries, South Bend, Ind.). Preferably, the aluminum alloys should have low copper and low silicon content. Coating thickness should be about 0.002 in., but can range from about 0.0004 to about 0.002 and preferably 0.0004 to about 0.0006 inches. In the case of a plastic mold, the coating is most preferably a permanent release surface such as a crosslinked silicone polymer.

The molds should be filled using a positive displacement metering pump capable of delivering precise amounts of liquid. Two examples of such pumps are an Oakes Mixer Model No. #2MT.5A and a Cozzoli Model F420X liquid filler. The operation of the Oakes Mixer is described in U.S. Pat. No. 5,354,558. It can deliver both a solution or a dispersion and can, with the correct formulations, generate a liquid foam. The liquid dispersion is fed to a positive displacement pump and transmitted through a line to a mixing chamber consisting of a rotor and stator. If foam is to be generated, an air line is activated, the air line being located in front of the mixing head. From the mixing head, the homogenous foam or dispersion/solution is delivered through an outlet pipe. The precise volume can be controlled by graduated markings in the mold or cartridge or the available volume.

The Cozzoli F420X is a syringe pump filler. When this filler is used, the liquid is drawn into the manifold through an inlet hose by the pumping action of the syringe. The length of the stroke and the available volume in the syringe control the volume of liquid. The length of the stroke is controlled by a knob setting. Foam cannot be generated.

After filling the cartridges with liquid, the samples are then freeze-dried in a Virtis 800L/Freezemobile 12, as set forth in U.S. Pat. No. 5,354,558. Filled molds are placed on the shelves of the drier which are chilled to from about −20° to about −50° C., preferably around −40° C. The condenser is set to from about −50° to about −70° C., preferably around −65° C. After the samples have been frozen and the temperatures reach from about −20° C. to about −40° C. as measured by thermocouples placed in the product, the pressure above the aqueous formulation is reduced, i.e., a vacuum is established. Once the vacuum has equilibrated over the period of one to two hours, the temperature of the shelves is raised and the ice is sublimed. The product is dried until the product temperature returns to about 20° to about 25° C. To shorten the drying time, the product temperature can be raised. The limitation is the phase transition termperature of the frozen formulation. If the product temperature exceeds the phase transition termperature, the formulation will "melt back" and the dried product will be more friable. Another method to decrease the drying time is to increase the vapor pressure in the chamber by bleeding in small amounts of air through a controlled system. The additional air aids in the convection heating of the samples. The limitation is that at too high a vapor pressure the sublimation efficiency of the ice will be reduced. In some examples listed below, vapor pressure was increased and, as a result, the drying time was decreased.

Most preferably, the cardboard cartridges should be placed in release-coated molds with a bullet-nosed cavity. The tip of the dried suppository will then extend beyond the cartridge, allowing for easier usage.

The length and width of the cartridge and/or suppository should be determined by the length and diameter required for insertion in the vagina or other body cavity and the space available in the drier. Preferably, for vaginal use, a suppository length of from about 1 to about 2" and a diameter of from about ⅛ to about ½" is appropriate. Most preferably, the suppository should be between about 1¼" and about 1½" long and have a diameter of about ⅜". Disposable cardboard cartridges can be from about 2 to about 4" in length and should have an internal diameter consistent with the intended suppository diameter. Most preferably, the cartridges should be about 3¾" in length.

In one embodiment, the products of this invention can be manufactured using miconazole nitrate as the active ingredient in a hydroxypropylmethylcellulose matrix. Generally, any other active ingredient that is known to those of ordinary skill in the art as being amendable to delivery in a lyophilized foam form in accordance with the procedures of this invention. Similarly, other water-soluble polymers, such as those set forth above, may also be used as matrices for the suppositories of the products of this invention.

The following examples illustrate the embodiment of the invention, however, they do not limit its use within the entire spirit and scope.

UNIT DOSE CARTRIDGE MATERIALS EVALUATION

A liquid dispersion was prepared by dispersing a blend of 144.4 g miconazole nitrate and 100.0 g hydroxypropylmethylcellulose (Methocel E50 LV Premium) in 1755.6 g of water previously heated to 180° F. After the dispersion was stirred for thirty minutes at 180° F., it was cooled to room temperature. A Cozzoli F420X filler was then assembled and several cartridge materials were filled from the Cozzoli F420X filler. The cartridge materials were as follows: (1) barrels cut from disposable cardboard applicator with rubber grommets; (2) polypropylene centrifuge tubes; (3) 3-cc B-D (Becton-Dickinson) syringes; and (4) aluminum suppository shell.

The samples were then placed on the selves of a Virtis 800L freeze-drier, temperature thermocouples were inserted and the products were frozen to −20° to −40° C. A vacuum was activated and maintained at 50 microns for 1 hour. The drying cycle was activated by applying heat to the drier shelves and the samples were lyophilized to 20° to 25° C. over an 18-hour period. All products could be removed from their cartridges at the end of the drying cycle. Experiments were conducted to evaluate different cartridge materials, mold materials and lyophilization conditions. These experiments are summarized in Table I and are more detailed in the following paragraphs.

TABLE I

| Example | Cartridge | Initial Vacuum (μm Hg) | Drying Time (Hours) | Support |
| --- | --- | --- | --- | --- |
| 1 | plastic syringe barrel | 45 | 47 | metal mesh |
| 2 | disposable cardboard applicator barrel | 50 | 47 | metal mesh |
| 3 | plastic syringe barrel | 300 | 23 | metal mesh |
| 4 | disposable cardboard applicator barrel | 300 | 23 | metal mesh |
| 5 | disposable cardboard applicator barrel | 600 | 24 | metal mesh |
| 6 | disposable cardboard applicator barrel | 900 | 22.5 | metal mesh |
| 7 | disposable cardboard applicator barrel | 30 | 17 | coated aluminum mold |

EXAMPLE 1

Plastic Cartridge From a Plastic Syringe Barrel

A liquid dispersion was prepared by dispersing a blend of 361 g miconazole nitrate and 250 g hydroxypropylmethylcellulose in 4389 g of water previously heated to 180° F. After the dispersion was stirred for thirty minutes at 180° F., it was cooled to room temperature. A Cozzoli F420X filler was then assembled and plastic barrels were placed in a metal mesh holder. The barrels were cut from plastic syringes and rubber grommets were inserted in the base to provide a sealed base for filling. The sample cartridges were then filled with about 2 cc of liquid product from the Cozzoli filler and placed on the shelves of a Virtis 800L freeze-drier. The samples were frozen to −20° to −40° C. A vacuum was activated and maintained at 45 microns for 1 hour. The drying cycle was activated and the samples were lyophilized to 20° to 25° C. over a 47-hour period. The products released easily from the barrels by pushing at the end of the grommet with a syringe plunger.

EXAMPLE 2

Cardboard Cartridge Cut from a Barrel of a Disposable Cardboard Applicator

A liquid dispersion was prepared by dispersing a blend of 361 g miconazole nitrate and 250 g hydroxypropylmethylcellulose in 4389 g of water previously heated to 180° F. After the dispersion was stirred for thirty minutes at 180° F., it was cooled to room temperature. A Cozzoli F420X filler was then assembled and cardboard barrels were placed in a metal mesh holder. The barrels were cut from cardboard applicators and rubber grommets were inserted in the base to provide a sealed base for filling. The sample cartridges were then filled from the Cozzoli filler and placed on the shelves of a Virtis 800L freeze-drier. The samples were frozen to −20° to −400° C. A vacuum was activated and maintained at 50 microns for 1 hour. The drying cycle was activated and the samples were lyophilized to 20° to 25° C. over a 47-hour period. The products released easily from the barrels by pushing at the end of the grommet with a cardboard plunger.

EXAMPLE 3

Plastic Cartridge From a Plastic Syringe Barrel

A liquid dispersion was prepared by dispersing a blend of 361 g miconazole nitrate and 250 g hydroxypropylmethylcellulose in 4389 g of water previously heated to 180° F. After the dispersion was stirred for thirty minutes at 180° F., it was cooled to room temperature. A Cozzoli F420X filler was then assembled and plastic barrels were placed in a metal mesh holder. The barrels were cut from plastic syringes and rubber grommets were inserted in the base to provide a sealed base for filling. The sample cartridges were then filled with about 2 cc of liquid product from the Cozzoli filler and placed on the shelves of a Virtis 800L freeze-drier. The samples were frozen to −20° to −40° C. A vacuum was activated and maintained at 300 microns for 1 hour. The drying cycle was activated and the samples were lyophilized to 20° to 25° C. over a 23-hour period. The products released easily from the barrels by pushing at the end of the grommet with a syringe plunger.

EXAMPLE 4

Cardboard Cartridge From a Cardboard Applicator Barrel

A liquid dispersion was prepared by dispersing a blend of 361 g miconazole nitrate and 250 g hydroxypropylmethylcellulose in 4389 g of water previously heated to 180° F. After the dispersion was stirred for thirty minutes at 180° F., it was cooled to room temperature. A Cozzoli F420X filler was then assembled and cardboard barrels were placed in a metal mesh holder. The barrels were cut from cardboard applicators and rubber grommets were inserted in the base to provide a sealed base for filling. The sample cartridges were then filled from the Cozzoli filler and placed on the shelves of a Virtis 800L freeze-drier. The samples were frozen to −20° to 40° C. A vacuum was activated and maintained at 300 microns for 1 hour. The drying cycle was activated and the samples were lyophilized to 20° to 25° C. over a 23-hour period. Using a vacuum level controller the vacuum was maintained at 300 microns throughout the drying cycle. The products released easily from the barrels by pushing at the end of the grommet with a cardboard plunger.

EXAMPLE 5

Cardboard Cartridge From a Cardboard Applicator Barrel

A liquid dispersion was prepared by dispersing a blend of 361 g miconazole nitrate and 250 g hydroxypropylmethylcellulose in 4389 g of water previously heated to 180° F. After the dispersion was stirred for thirty minutes at 180° F., it was cooled to room temperature. A Cozzoli F420X filler was then assembled and cardboard barrels were placed in a metal mesh holder. The barrels were cut from cardboard applicators and rubber grommets were inserted in the base to provide a sealed base for filling. The sample cartridges were then filled from the Cozzoli filler and placed on the shelves of a Virtis 800L freeze-drier. The samples were frozen to −20° to −40° C. A vacuum was activated and maintained at 600 microns for 1 hour. The drying cycle was activated and the samples were lyophilized to 20° to 25° C. over a 24-hour period. Using a vacuum level controller the vacuum was maintained at 600 microns throughout the drying cycle. The products released easily from the barrels by pushing at the end of the grommet with a cardboard plunger.

EXAMPLE 6

Cardboard Cartridge From a Cardboard Applicator Barrel

A lyophilized product was formed in situ in accordance with the procedure set forth in Example 5, however, the vacuum was set at 900µ and drying conducted over a 22.5 hour period. The products released easily from the barrels by pushing at the end of the grommet with a cardboard plunger.

EXAMPLE 7

Cardboard Cartridge From a Cardboard Applicator Barrel Made in Coated Aluminum Molds A liquid dispersion was prepared by dispersing a blend of 361 g miconazole nitrate and 250 g hydroxypropylmethylcellulose in 4389 g of water previously heated to 180° F. After the dispersion was stirred for thirty minutes at 180° F., it was cooled to room temperature. A Cozzoli F420X filler was then assembled and cardboard barrels were placed in aluminum molds coated with Teflon® polytetrafluoroethylene-impregnated hard anodized release coating. The mold cavities were bullet-shaped. The barrels were cut from cardboard applicators and were inserted into the bullet-shaped mold cavities. The sample cartridges were then filled from the Cozzoli filler and placed on the selves of a Virtis 800L freeze-drier. The samples were frozen to −20° to −40° C. A vacuum was activated and maintained at 30 microns for 1 hour. The drying cycle was activated and the samples were lyophilized to 20° to 25° C. over a 17-hour period. The products were removed from the mold and the dried product could be ejected from the cartridges with a plunger.

What is claimed is:

1. A method for making a suppository in a unit-dose applicator comprising the following steps:
    (a) placing a tubular cartridge in a cartridge-holder;
    (b) filling said tubular cartridge with an aqueous composition;
    (c) freezing said aqueous composition to a temperature between about −20° and about −40° C.;
    (d) reducing pressure above the frozen aqueous composition to an absolute pressure in the range of about 30 microns Hg to about 1000 microns Hg; and
    (e) drying said composition in said tubular cartridge.

2. A method according to claim 1 wherein said tubular cartridge comprises a material selected from the group consisting of: plastic, metal and cardboard.

3. A method according to claim 2 wherein said tubular cartridge is cardboard.

4. A method according to claim 1 wherein said aqueous composition comprises a treatment composition comprising a water-dispersible polymer and a pharmaceutically active ingredient.

5. A method according to claim 4 wherein said water-dispersible polymer is a cellulose ether compound.

6. A method according to claim 5 wherein said cellulose ether compound is selected from the group consisting of: hydroxypropylmethylcellulose, sodium carboxymethylcellulose, methylcellulose, hydroxyethylcellulose, hydroxypropylcellulose, hydroxyethylmethylcellulose, hydroxyethylethylcellulose, hydroxypropylethylcellulose, Carbopol, polyvinyl alcohol and derivatives thereof, dextran, chitosan and its derivatives, starch and its derivatives, polyacrylamides, polyacrylates, agar, collagen, fibronectin, alginic acid, pectin, hyaluronic acid or mixtures thereof.

7. A method according to claim 5 wherein said polymer is hydroxypropylmethylcellulose.

8. A method according to claim 1 wherein said holder is a metal mesh.

9. A method according to claim 1 wherein said holder is a metal mold.

10. A method according to claim 9 wherein said metal mold comprises aluminum.

11. A method according to claim 10 wherein said metal mold comprises aluminum containing a release coating.

12. A method according to claim 11 wherein said release coating is polytetrafluoroethylene.

13. A method according to claim 1 wherein the pressure above the frozen aqueous formulation is greater than 300 µHg.

14. A method according to claim 13 wherein the pressure above the frozen aqueous formulation is greater than 600 µHg.

15. A method according to claim 1 wherein said pressure is reduced above said frozen aqueous formulation for a period of at least one hour.

16. A method according to claim 1 wherein said vacuum is maintained throughout steps (d) and (e).

17. A method according to claim 1 wherein said compositions are dried for at least 40 hours.

18. A method according to claim 1 wherein said compositions are dried for between about 20 and about 30 hours.

19. A suppository in a unit dose applicator made according to the method of claim 1.

20. A method according to claim 1 wherein said holder is a plastic mold.

21. A method according to claim 20 wherein said mold contains a release coating.

22. A method according to claim 21 wherein said release coating is a permanent release coating.

23. A method according to claim 22 wherein said release coating comprises a crosslinked silicone polymer.

24. A suppository according to claim 19 comprising miconazole nitrate.

* * * * *